(12) United States Patent
Harlan et al.

(10) Patent No.: US 7,050,692 B2
(45) Date of Patent: May 23, 2006

(54) PROXIMAL COUPLER FOR OPTICAL FIBERS

(75) Inventors: Kenneth D. Harlan, Peyton, CO (US); Kenneth P. Grace, Woodland Park, CO (US); Robert Carver, Colorado Springs, CO (US); Michael Sean Coe, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 67 days.

(21) Appl. No.: 10/301,937

(22) Filed: Nov. 22, 2002

(65) Prior Publication Data

US 2003/0185523 A1 Oct. 2, 2003

Related U.S. Application Data

(60) Provisional application No. 60/368,725, filed on Mar. 29, 2002.

(51) Int. Cl.
*G02B 6/00* (2006.01)

(52) U.S. Cl. .................. 385/136; 385/137; 385/116; 385/117; 385/88; 385/92; 385/53; 385/54; 385/76; 385/77

(58) Field of Classification Search ............... 385/88, 385/81, 85, 86, 139, 136, 137, 92, 76, 77, 385/78, 83, 87, 116, 117, 53, 54
See application file for complete search history.

(56) References Cited

U.S. PATENT DOCUMENTS

| 4,478,485 A * | 10/1984 | Khoe et al. ............... 385/53 |
|---|---|---|
| 4,515,434 A * | 5/1985 | Margolin et al. ............. 385/65 |
| 5,373,572 A * | 12/1994 | Arkwright et al. ............ 385/43 |
| 5,404,415 A * | 4/1995 | Mori et al. .................... 385/43 |
| 5,454,056 A * | 9/1995 | Brothers ....................... 385/16 |
| 5,742,718 A * | 4/1998 | Harman et al. ............... 385/53 |
| 5,971,628 A * | 10/1999 | Dona et al. ................... 385/88 |
| 6,027,461 A * | 2/2000 | Walker et al. .............. 600/585 |
| 6,065,882 A * | 5/2000 | Roller et al. .................. 385/92 |
| 6,217,205 B1 * | 4/2001 | Ward .......................... 362/580 |
| 6,325,549 B1 * | 12/2001 | Shevchuk ..................... 385/86 |
| 6,419,405 B1 * | 7/2002 | Boscha ......................... 385/93 |
| 6,456,766 B1 * | 9/2002 | Shaw et al. ................... 385/47 |
| 6,626,582 B1 * | 9/2003 | Farrar et al. .................. 385/53 |
| 2002/0037142 A1 * | 3/2002 | Rossi .......................... 385/92 |
| 2002/0181882 A1 * | 12/2002 | Hibbs-Brenner et al. ...... 385/52 |
| 2003/0002825 A1 * | 1/2003 | Karker et al. ................. 385/92 |
| 2003/0012522 A1 * | 1/2003 | Johnson ....................... 385/91 |

(Continued)

*Primary Examiner*—Thien M. Le
*Assistant Examiner*—Allyson N Trail
(74) *Attorney, Agent, or Firm*—Rader, Fishman & Grauer PLLC; James F. Kamp, Esq.

(57) ABSTRACT

A coupler for interfacing a light source, such as a laser, and a fiber optic cable is disclosed. The coupler includes a slide mount having a channel that is adapted to receive optical fibers. The channel extends from a proximal end of the slide mount to a distal end of the slide mount. The proximal end of the slide mount is adapted to fit into an aperture of the light source and the distal end of the slide mount is adapted to transmit light to the fiber optic cable. The coupler also includes a clamp that is mounted on the slide mount adjacent to its proximal end. The clamp covers at least a portion of the channel, thereby securing the optical fibers within the channel without the use of an adhesive.

26 Claims, 7 Drawing Sheets

U.S. PATENT DOCUMENTS

| | | | |
|---|---|---|---|
| 2003/0053763 A1* | 3/2003 | Goto | 385/88 |
| 2003/0063868 A1* | 4/2003 | Fentress | 385/78 |
| 2003/0063888 A1* | 4/2003 | Sahlin et al. | 385/134 |
| 2003/0077043 A1* | 4/2003 | Hamm et al. | 385/72 |
| 2003/0147601 A1* | 8/2003 | Bartur et al. | 385/92 |
| 2003/0147604 A1* | 8/2003 | Tapia et al. | 385/101 |
| 2003/0165300 A1* | 9/2003 | Greub et al. | 385/80 |
| 2004/0131325 A1* | 7/2004 | Mueller et al. | 385/134 |

* cited by examiner

PROXIMAL COUPLER FOR OPTICAL FIBERS

This application claims priority to U.S. Provisional Application Ser. No. 60/368,725, filed on Mar. 29, 2002.

FIELD OF THE INVENTION

The present invention relates to optical waveguides that employ mechanical connectors for coupling a light source to the waveguide, and more particularly, to mechanical couplers for terminating optical fibers of catheters used in laser angioplasty and other medical procedures.

DISCUSSION

Numerous medical procedures require delivery of energy from a light source, such as a laser, through optical fibers or similar waveguides that are disposed in the body. These medical procedures include removal of arterial plaque and occlusions (laser angioplasty), extraction of cardiac pacemaker leads, destruction of tumors and calculi, and repair of bleeding vessels. The optical fibers used in the medical procedures are disposed within a flexible tube or catheter, which slides over a guide wire for routing the catheter from an entry point to a treatment area in the body. Lasers used in the medical procedures may generate either pulsed or continuous light having wavelengths ranging from the ultraviolet region of the electromagnetic spectrum to the infrared region.

Light delivery systems used in medical treatment and diagnosis also include connectors that couple the light source to the optical fibers. Such connectors are called "proximal" couplers because they are located adjacent to the light source—a "distal" system component would be located further away from the light source. Proximal couplers typically comprise a grip or handle and a slide mount, which extends outward from the handle portion of the coupler. The slide mount fits into an aperture or slot in the light source and includes an open channel or groove that extends from the handle portion of the coupler to an end region. In many designs the channel, when viewed on end, has a rectangular, square, or round shape that is adapted to receive a bundle of optical fibers, which also has a rectangular, square, or round cross section. Current couplers employ an adhesive to secure the optical fiber bundle in the channel.

The use of an adhesive may adversely affect the performance of the proximal coupler. For example, care is taken during assembly of the proximal coupler to ensure that the adhesive is placed away from the ends of the optical fiber. However, some of the adhesive often flows along the surface of the optical fiber bundle or between individual fibers. Any adhesive that migrates to the ends of the optical fibers may preferentially absorb radiant energy from the light source, resulting in local hot spots that can damage the optical fibers. Furthermore, when the adhesive flows unevenly into air gaps in the fiber bundle, it may displace individual fibers, which causes inconsistent fiber packing among couplers.

The use of adhesives leads to other problems as well. Once the adhesive has hardened or cured, it is difficult to remove without damaging the optical fibers and the slide mount, which renders any rework of the proximal coupler problematic. Furthermore, the adhesive may take twenty minutes or more to harden, which adds to production costs. Finally, because of the rigorous design requirements of proximal couplers, few adhesives have been found acceptable for securing the optical fibers in place. In some cases, manufacturers of proximal couplers must rely on a single source for the adhesive, which makes the manufacturer vulnerable to disruptions in supply.

The present invention is directed to overcoming, or at least reducing, the effects of one or more of the problems discussed above.

SUMMARY OF THE INVENTION

The present invention provides a proximal coupler for interfacing a light source, such as a laser, and a fiberoptic cable. The coupler comprises a slide mount, which has a channel that is adapted to receive optical fibers. The channel extends from a point at or adjacent to the proximal end of the slide mount to a distal end of the slide mount. The proximal end of the slide mount is sized and configured to fit into an aperture of the light source and the distal end of the slide mount is sized and configured to transmit light to the fiber optic cable. The coupler also includes a clamp that is mounted on the slide mount adjacent to its proximal end. The clamp covers at least a portion of the channel, thereby securing the optical fibers within the channel without having to use an adhesive. Alternatively or additionally, the coupler may include a capillary tube that is attached at or near the proximal end of the slide mount. The capillary tube is disposed within the channel, and like the clamp, secures the optical fibers without having to use an adhesive.

A second aspect of the present invention provides a method of making a coupler for interfacing a light source and a fiber optic cable. The method comprises providing a slide mount having a channel that is adapted to receive optical fibers. The channel extends from a point at or near the proximal end of the slide mount to a distal end of the slide mount. The proximal end of the slide mount is adapted to fit into an aperture of the light source and the distal end of the slide mount is adapted to transmit light to the fiber optic cable. The method also includes disposing optical fibers in the channel of the slide mount so that the optical fibers extend from the distal end of the slide mount to the proximal end of the slide mount, and mounting a clamp on the slide amount adjacent to its proximal end, so that the clamp covers at least a portion of the channel. In another embodiment, the method also includes disposing optical fibers in the channel of the slide mount so that the optical fibers extend from the distal end of the slide mount to the proximal end of the slide mount, disposing at least a portion of the optical fibers within a capillary tube, disposing the capillary tube within the channel; and securing the capillary tube at or adjacent to the proximal end of the slide mount, thereby securing the optical fibers within the channel. In this way, the optical fibers are secured within the channel without having to use an adhesive.

The use of a clamp, a capillary tube, or clamp and a capillary tube provides certain advantages over conventional couplers that employ adhesives to secure the optical fibers. For example, removal of the adhesive should eliminate any damage to the optical fibers resulting from local heating of the adhesive. Removal of the adhesive should also result in more consistent fiber packing among couplers since the dimensions of the passageway defined by the capillary tube or by the walls of the channel and the clamps can be controlled to close tolerances. Furthermore, the coupler can be easily reworked if necessary, because the optical fibers can be quickly removed by disconnecting the clamp or by extracting the capillary tube. Eliminating the adhesive should reduce time and labor costs associated with applying the adhesive and should obviate any difficulties associated with interruptions in the supply of the adhesive.

BRIEF DESCRIPTION OF THE DRAWINGS

The various features, advantages and other uses of the present invention will become more apparent by referring to the following description and drawings in which.

DETAILED DESCRIPTION

Figure 1:
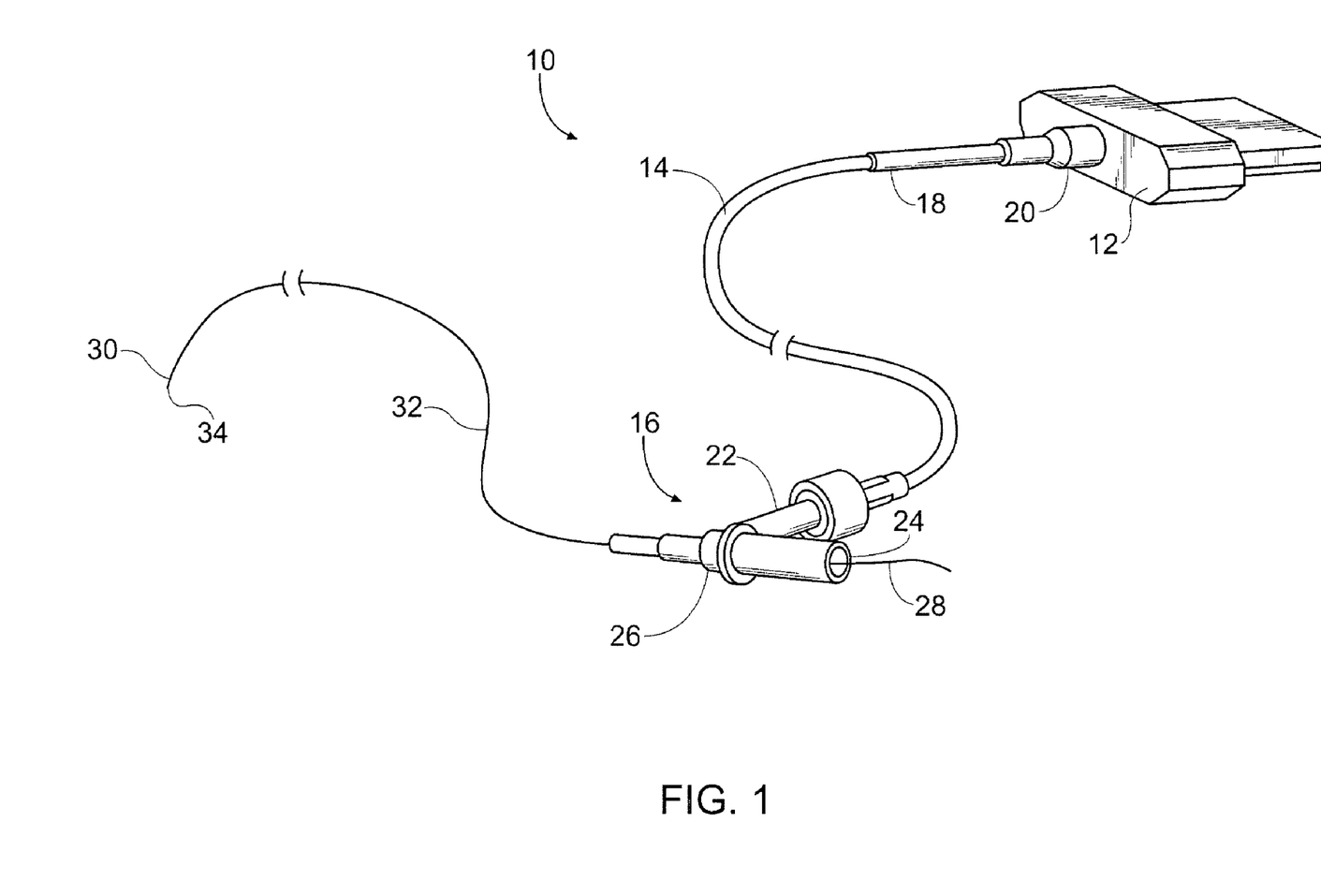
FIG. 1 is a perspective view of a fiber optic-catheter assembly and proximal coupler.

FIG. 1 is a perspective view of a fiber optic-catheter assembly 10 and proximal coupler 12. As noted earlier, the proximal coupler provides an interface between the fiber optic-catheter assembly 10 and a light source (e.g., laser, not shown). The assembly 10 includes a light conveying cable 14, which contains optical fibers that direct light from the proximal coupler 12 to a bifurcating adapter 16. A proximal end 18 of the cable 14 includes a strain relief sleeve 20, which is typically made of coiled metal or an elastomer and helps reduce damage to the assembly 10 due to forces exerted on the cable 14 during handling. Note that throughout the specification the terms "proximal" and "distal" refer to the location of a component of the assembly 10 relative to the light source-a component that is nearer to the light source is "proximal," whereas a component that is further away from the light source is "distal."

As shown in FIG. 1, the bifurcating adapter 16 includes a pair of branches 22, 24 that converge into a single trunk 26. One of the branches 22 receives the light conveying cable 14, while the other branch 24 receives a guide wire 28, which is used to route the distal end 30 of the fiber optic-catheter assembly 10 from an entry point in the body to a treatment area. The trunk 26 of the bifurcating adapter 16 receives a catheter 32, which generally comprises an outer tube and an inner tube (not shown). The annular region between the outer tube and the inner tube defines an outer lumen, which contains optical fibers, and the interior of the inner tube defines an inner lumen that contains the guide wire 28. The inner and outer tubes may be constructed from any of a number of suitable materials, including plasticized vinyl resins, polyethylene, polytetrafluoroethylene, synthetic and natural rubbers and polyurethane elastomers. The distal end 30 of catheter 32 terminates at a tip 34, which is adapted to deliver light to the treatment area.

Figure 2:
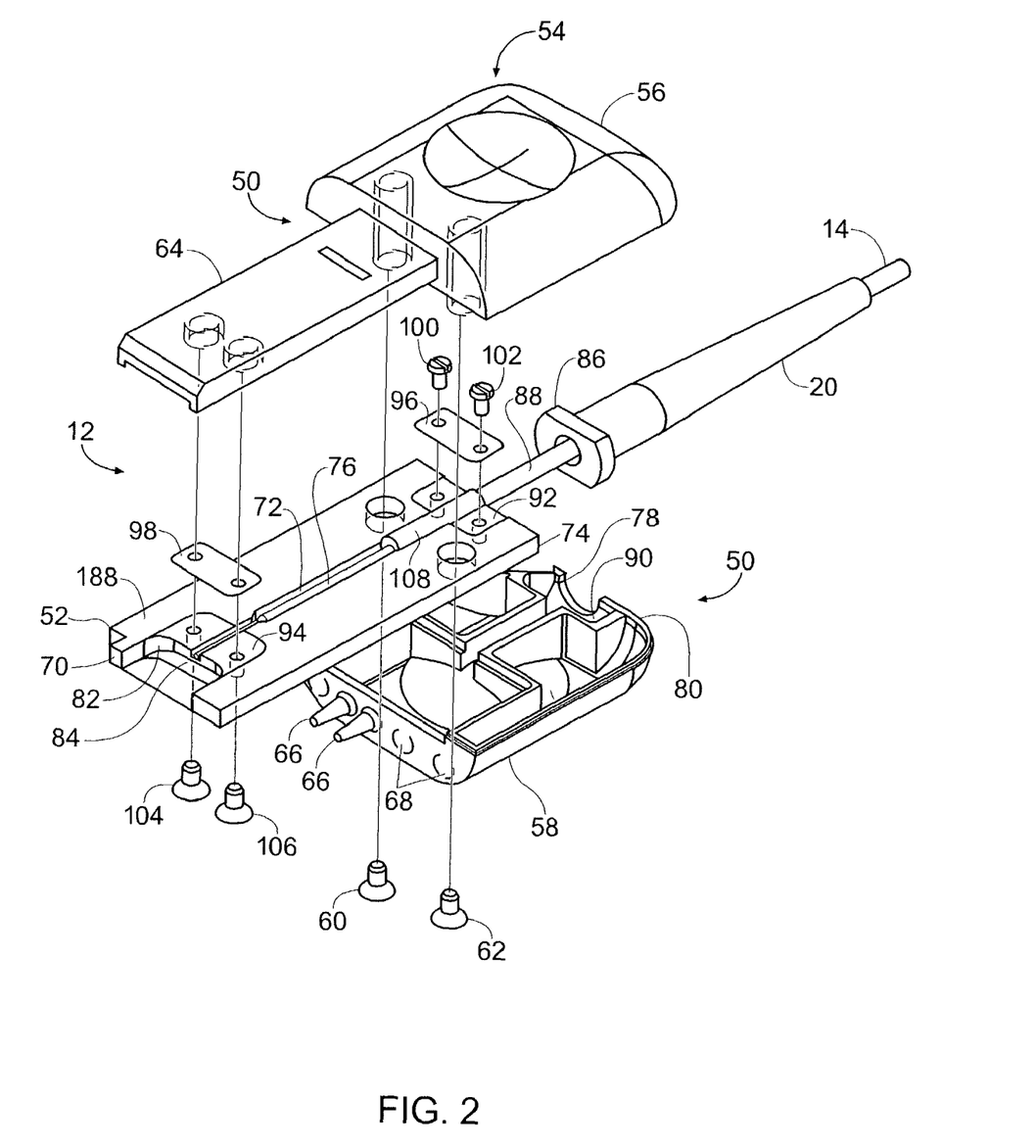
FIG. 2 is an exploded view of a proximal coupler, which utilizes hold down clamps to secure optical fibers.

FIG. 2 is an exploded view of one embodiment of a proximal coupler 12, which utilizes hold down clamps to secure optical fibers from the light conveying cable 14. The proximal coupler 12 comprises a housing 50 and a slide mount 52, which extends outward from a handle region 54 of the housing 50. The slide mount 52 is disposed between first 56 and second 58 portions of the housing 50, which are joined together using threaded fasteners 60, 62. In other embodiments, the two portions 56, 58 of the housing 50 may be joined together using snap tabs that project from one portion of the housing 50 and which mate with corresponding holes in the other portion of the housing 50 or by bonding the two portions 56, 58 of the housing 50 together using adhesives or ultrasound welding techniques, as described, for example, in U.S. Pat. No. 5,321,783 to Nielson et al., which is herein incorporated by reference in its entirety and for all purposes. The first 56 and second 58 portions of the housing 50 are typically fabricated of materials having comparatively high modulus, including metals (aluminum, steel, etc.) and thermoplastics (filled and unfilled polymers, including acetal homopolymers, polyvinyl chloride, polycarbonate, polyamide, and the like).

The handle region 54 of the two portions 56, 58 of the housing 50 are similar, but the first portion 56 of the housing 50 also includes a cover 64, which extends outward from the handle region 54 and is sized and configured to cover at least some of the slide mount 52. Additionally, the second portion 58 of the housing 50 includes one or more pins 66 and holes 68 that provide the light source (laser) with information concerning the nature of the catheter 32, such as its size, fluence damage threshold, etc. The use of pins 66 and holes 68 is discussed in U.S. Pat. No. 4,919,508 to Grace et al., which is herein incorporated by reference in its entirety and for all purposes.

As noted above, a proximal end 70 of the slide mount 52 fits into an aperture or slot in the light source. The slide mount 52 includes an open channel 72 or groove that runs from a distal end 74 of the slide mount 52 to the proximal end 70 of the slide mount 52. The open channel 72, when viewed from the proximal 70 end of the slide mount 52, has a rectangular, square, or round shape that is sized to receive a bundle of optical fibers 76 also having a rectangular, square, or round cross section. The slide mount 52 is typically fabricated from a material having a relatively high modulus, including for example and without limitation, metal (e.g., aluminum, stainless steel, etc.) and engineered thermoplastics, which are compatible with the light source. For a discussion of suitable cross-sectional areas of the bundle of optical fibers 76, see U.S. Pat. No. 5,315,614 to Grace et al., which is herein incorporated by reference in its entirety and for all purposes.

Thus, as shown in FIG. 2, the optical fibers 76 from the light conveying cable 14 enter the proximal coupler 12 through an aperture 78 formed in a distal end 80 of the housing 50, run the length of the channel 72, and terminate in a cavity formed by a notch 82 at the proximal end 70 of the slide mount 52. Since the proximal ends 84 of the fibers 76 extend into the cavity a few millimeters (e.g., 1 mm to 2 mm), there is less chance that laser light will damage the proximal end 70 of the slide mount 52. As indicated above, the cable 14 includes a strain relief sleeve 20, which as can be seen in FIG. 2, includes a flanged portion 86 at its proximal end 88 that fits into a slot 90 in the housing 50, thereby securing the strain relief sleeve 20 to the proximal coupler 12.

Still referring to FIG. 2, the slide mount 52 includes a pair of depressions 92, 94 located at its distal 74 and proximal 70 ends, which bracket the open channel 72 and which are sized and configured to receive a pair of clamps 96, 98 or hold-down tabs. The clamps 96, 98 are secured in place using threaded fasteners 100, 102, 104, 106 and serve to retain the optical fiber 76 within the channel 72. The optical fibers 76 adjacent to the distal end 74 of the slide mount 52, are contained within a polymeric shrink tube 108, which provides a buffer between the distal clamp 96 and the optical fibers 76. In contrast, the optical fibers located adjacent to the proximal end 70 of the slide mount 52 contain no sheathing and therefore may contact the proximal clamp 98. As indicated in FIG. 2, the proximal clamp 98 is recessed back from the notch 82 a small distance (e.g., 0.5 mm to 1 mm) which reduces the chance that laser light will damage the clamp 98. Generally, the clamps 96, 98 can be fabricated from the same materials used to make the slide mount 52, such as aluminum, stainless steel, and the like.

The use of clamps 96, 98 instead of an adhesive provides certain advantages over conventional proximal couplers. For example, removal of the adhesive should eliminate any damage to the optical fibers 76 resulting from local heating of the adhesive and should result in more consistent fiber packing among proximal couplers 12 since the dimensions of the passageway defined by the walls of the channel 72 and the clamps 96, 98 can be controlled to close tolerances. Furthermore, the proximal coupler 12 shown in FIG. 2 can be easily reworked if necessary, because the optical fibers 76 can be quickly removed by disconnecting the clamps 96, 98. Eliminating the adhesive should reduce time and labor costs associated with applying the adhesive and should remove difficulties associated with interruptions in the supply of the adhesive. Besides eliminating the application of the adhesive, use of the clamps 96, 98 should not require a change in the manufacture of the proximal coupler 12. For a description of a process for preparing and installing optical fiber in a proximal coupler, see U.S. Pat. No. 5,400,428 to Grace, which is herein incorporated by reference in its entirety and for all purposes.

Figure 3:
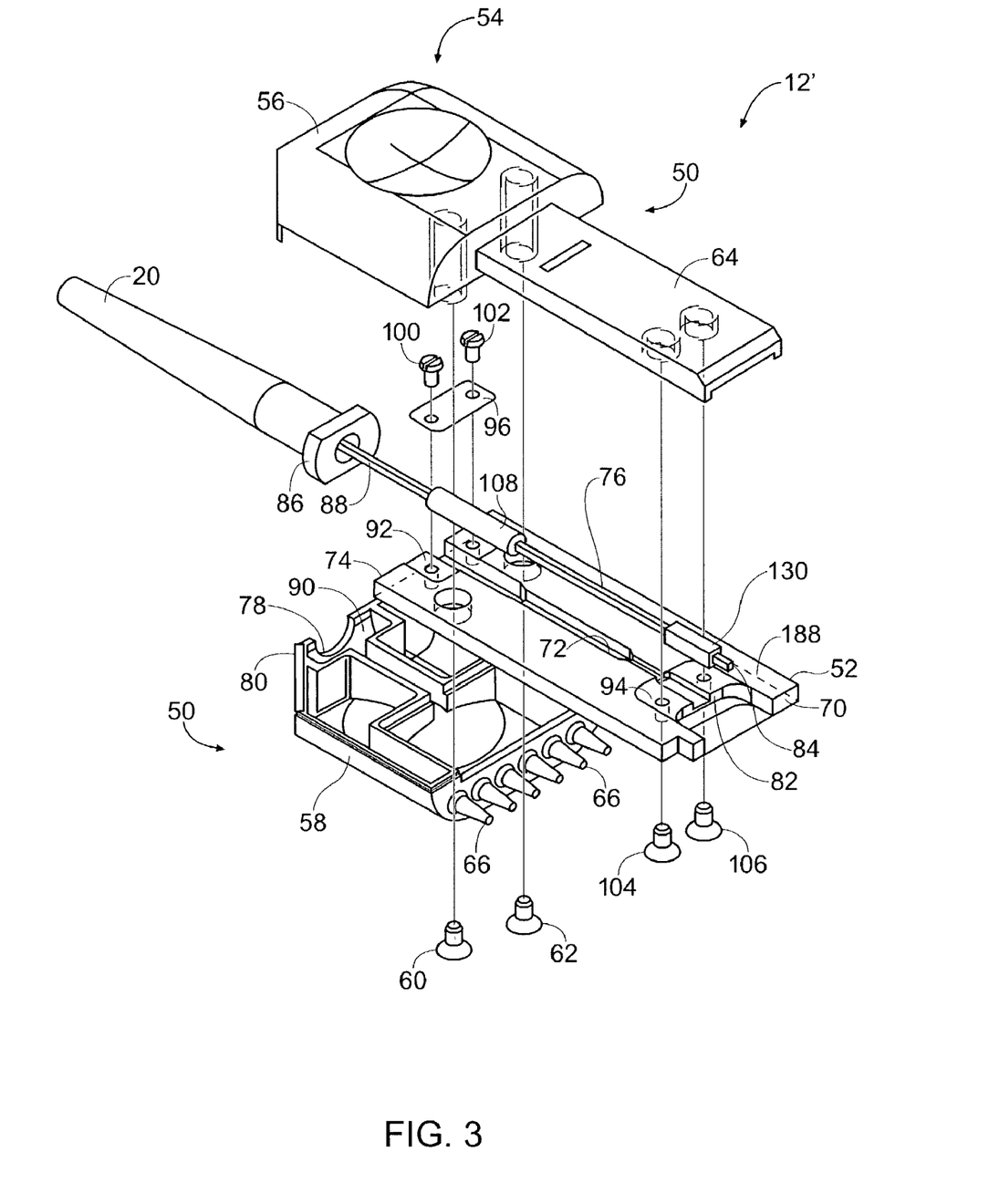
FIG. 3 is an exploded view of a proximal coupler, which utilizes a capillary tube to secure optical fibers.
Figure 4:
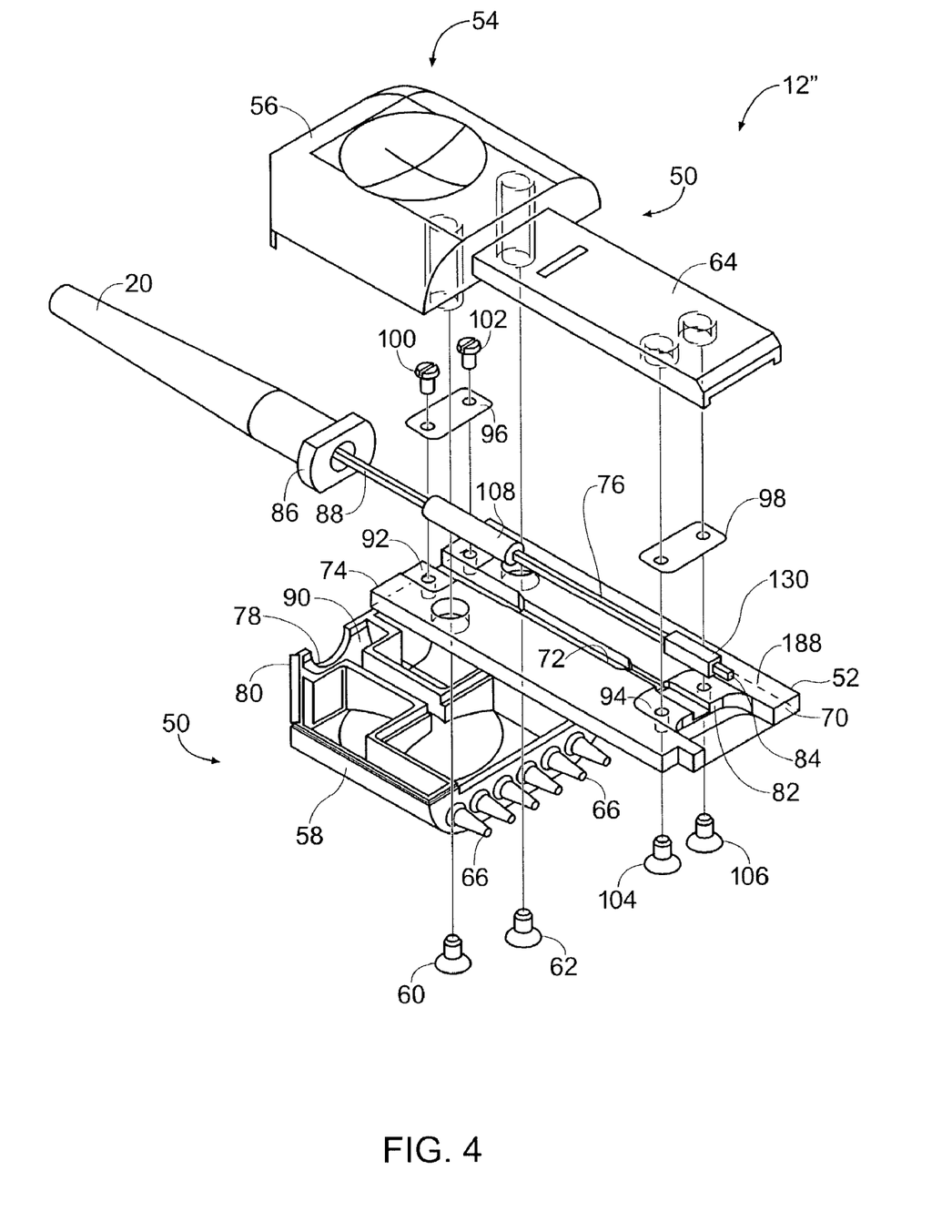
FIG. 4 is an exploded view of a proximal coupler, which utilizes a capillary tube and a hold down clamp to secure optical fibers.

FIG. 3 and FIG. 4 show additional embodiments of a proximal coupler 12', 12", which offer many of the same advantages as the coupler 12 shown in FIG. 2, but employ different mechanical devices for securing the optical fibers 76 in the channel 72. Since the optical fibers 76 and the channel 72 may be substantially the same as those shown in FIG. 2, all three figures use the same reference numbers to refer to the optical fibers 76 and the channel 72. More generally, like reference numbers refer to similar elements throughout the specification and the drawings.

Referring to FIG. 3 and to FIG. 4, both proximal couplers 12', 12" utilize a capillary tube 130 having a rectangular, square, or round cross-section, which is secured in the channel 72 at a location adjacent to the proximal end 70 of the slide mount 52. By using the capillary tube 130, both proximal couplers 12', 12" provide tighter control over the packing geometry of the optical fibers 76, which pass through the capillary tube 130. The two proximal couplers 12', 12" differ in the way the capillary tube 130 is secured in the channel 72. The proximal coupler 12' shown in FIG. 3 uses friction to secure the capillary tube 130 in the channel 72, while the proximal coupler 12" shown in FIG. 4 uses a proximal clamp 98.

Other embodiments of the proximal coupler 12, 12', 12" may use a single clamp that extends substantially over the length of the channel 72, or may use multiple channels 72 to contain multiple fiber optic bundles 76, or may replace the distal clamp 96 with elastomeric grommets and the like, to eliminate the need for the shrink tube 108. Although the proximal couplers 12, 12', 12" shown in FIG. 2 and FIG. 4 employ hold down clamps 96, 98 that are substantially planar, other embodiments may include clamps 96, 98 having different shapes.

Figure 5:
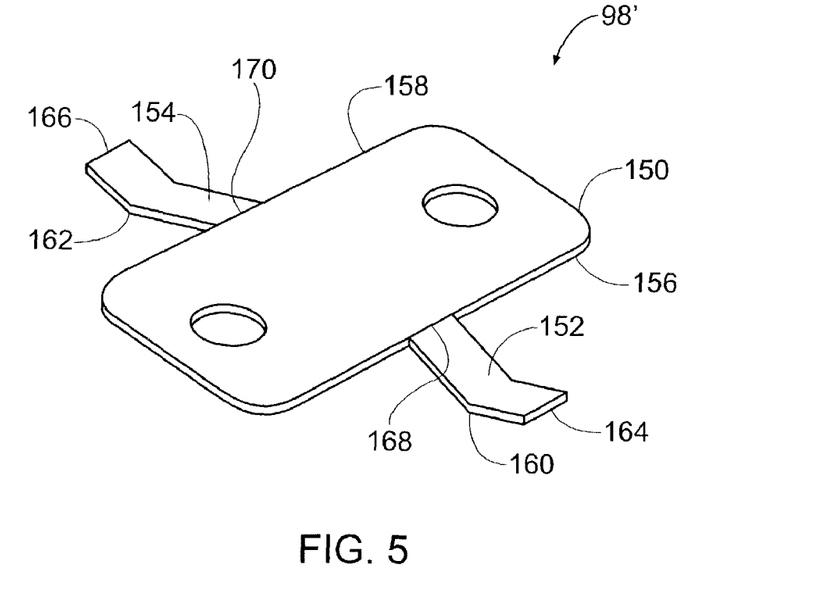
FIG. 5 is a perspective view of a cantilevered hold down clamp for securing optical fibers.
Figure 6:
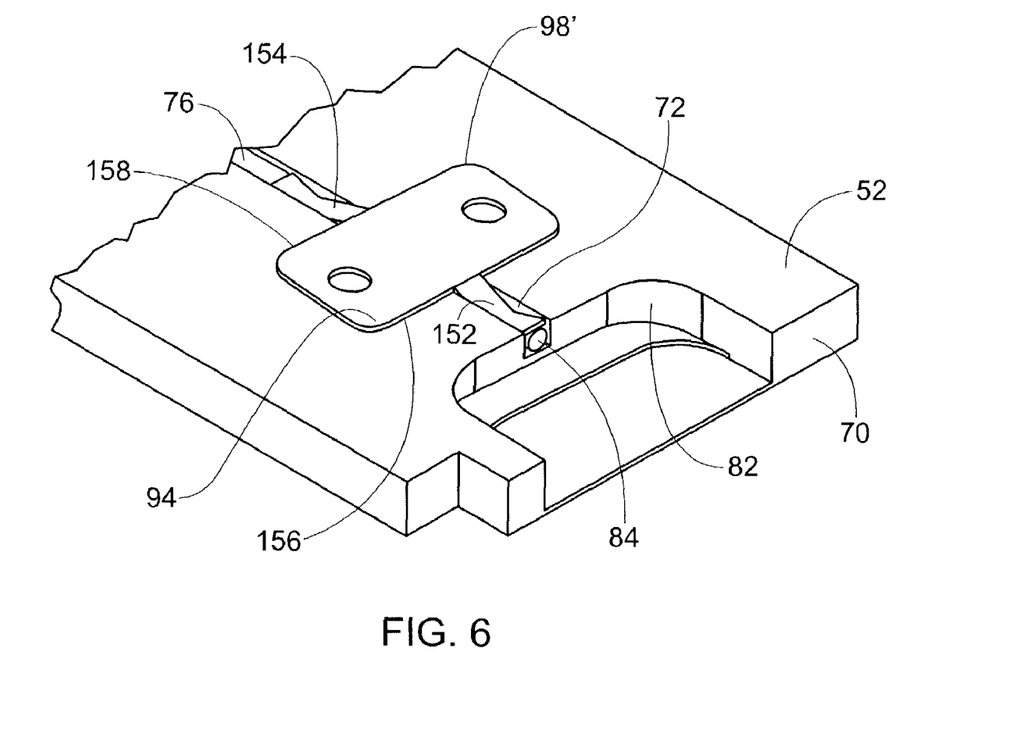
FIG. 6 is an exploded view of a proximal coupler, which utilizes the cantilevered hold down clamp shown in FIG. 5.
Figure 7:
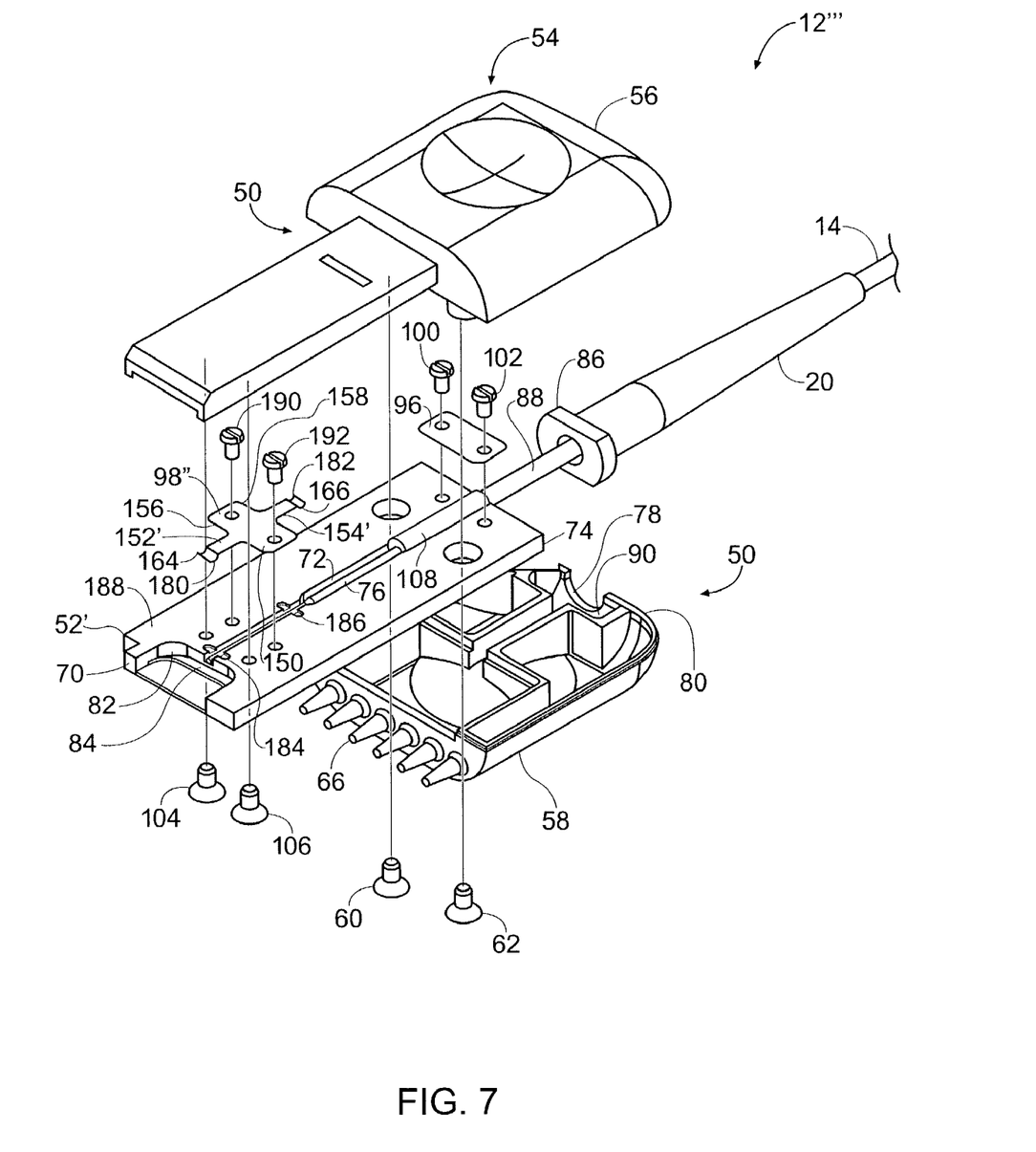
FIG. 7 is an exploded view of a proximal coupler, which utilizes a second embodiment of a cantilevered hold down clamp for securing optical fibers.

For example, FIG. 5, FIG. 6 and FIG. 7 show proximal hold down clamps 98', 98" employing cantilevered arms. One such clamp 98' is shown in FIG. 5 and FIG. 6. The clamp 98' has a substantially planar base 150 and a pair of arms 152, 154 that extend outward from the proximal 156 and distal 158 sides of the base 150. The arms 152, 154 intersect the base 150 at a non-zero angle and are sized so that, when the clamp 98' is installed in the depression 94 adjacent to the proximal end 70 of the slide mount 52, at least a portion of each arm 152, 154 extends below the plane of the base 150 and into the channel 72 that contains the bundle of optical fibers 76. The arms 152, 154 also include elbows 160, 162 that are located adjacent to the proximal 164 and distal 166 ends of the arms 152, 154 and which contact the optical fibers 76 in the channel 72.

The disclosed hold down clamps are typically fabricated from materials having comparatively high modulus, including for example and without limitation, metal (e.g., aluminum, stainless steel, etc.) and engineered thermoplastics. However, the thickness and width of the arms 152, 154 permit them to flex or pivot about lines 168, 170 that connect the arms 152, 154 and the base 150. In this way, the hold down clamp 98' shown in FIG. 5 and in FIG. 6 exerts pressure on the optical fibers 76 at the elbow 160, 162 portions of the arms 152, 154, which helps secure bundle of optical fibers 76 in the channel 72. One may tailor the pressure on the optical fibers 76 by, among other things, adjusting the material used to fabricated the proximal clamp 98', modifying the thickness of the arms 152, 154, and changing the location of the elbow portions 160, 162 of the arms 152, 154 relative to the flex lines 168, 170 (i.e., by adjusting the length of the lever arm).

FIG. 7 is an exploded view of a proximal coupler 12''', which includes a second embodiment of a cantilevered hold down clamp 98". Like the first embodiment, the proximal clamp 98" shown in FIG. 7 includes a substantially planar base 150 and a pair of arms 152', 154' that extend outward from the proximal 156 and distal 158 sides of the base 150. In contrast to the clamp 98' shown in FIG. 5 and FIG. 6, a substantial portion of the arms 152', 154' of the clamp 98" shown in FIG. 7 generally lie in the same plane as the base 150 and are wider than the slide mount 52' channel 72. To apply pressure on the optical fibers 72, the arms 152', 154' include arcuate contact portions 180, 182, which are located adjacent to the proximal 164 and distal 166 ends of the arms 152', 154'. The contact portions 180, 182 extend outward from the plane that contains the base 150 and much of the arms 152', 154' and fit into proximal 184 and distal 186 transverse grooves that intersect the channel 72. Although the width of the channel 72 may vary among proximal couplers, the size and location of the transverse grooves 184, 186 can be standardized. This allows the same clamp 98" to be used with all of the proximal couplers of a given manufacturer and should result in lower production costs.

The proximal hold down clamp 98" shown in FIG. 7 is mounted on a surface 188 of the slide mount 52' using a pair of threaded fasteners 190, 192, which are different than the threaded fasteners 104, 106 used to attach the slide mount 52' to the housing 50. Other embodiments may use the same fasteners for both purposes. Although the proximal coupler 12''' shown in FIG. 7 utilizes a cantilevered proximal hold down clamp 98" and a substantially planar or rectangular distal hold down clamp 96, the proximal coupler 12''' may also employ a cantilevered distal hold down clamp as well.

The cantilevered hold down clamps 98', 98" depicted in FIG. 5, FIG. 6 and FIG. 7 should result in more consistent packing of the optical fibers within the channel 72. Although the channel 72 is sized to accommodate a desired number of optical fibers 76, variations among the diameters of the optical fibers 76 and the dimensions of the channel 72 may result in excess volume in the channel 72. This may cause improper packing of the optical fibers 76, which results in the proximal ends 84 of the optical fibers 76 extending above the surface 188 of the slide mount 52 and therefore outside the path of the light source (e.g., laser). The cantilevered clamps 98', 98" apply substantially uniform and reproducible pressure on the optical fibers 76, which should result in more consistent fiber packing and thus better coupling of the light source and the optical fibers 76.

The proximal couplers 12, 12', 12", 12''' shown in FIG. 2–FIG. 7 utilize clamps 98, 98', 98" that are affixed to the slide mount 52, 52'. However, the proximal couplers may instead employ hold down clamps, which are integral parts of the proximal coupler housing 50. With suitable modification, the hold down clamps 98, 98', 98" may thus be attached to the cover portion 64 of the housing 50 using threaded fasteners, friction welding, adhesives, etc. Alternatively, the hold down clamps may be formed during fabrication (e.g., molding, machining) of the housing 50. The latter designs are advantageous because they reduce part count, thereby simplifying the assembly of the proximal coupler.

Figure 8:
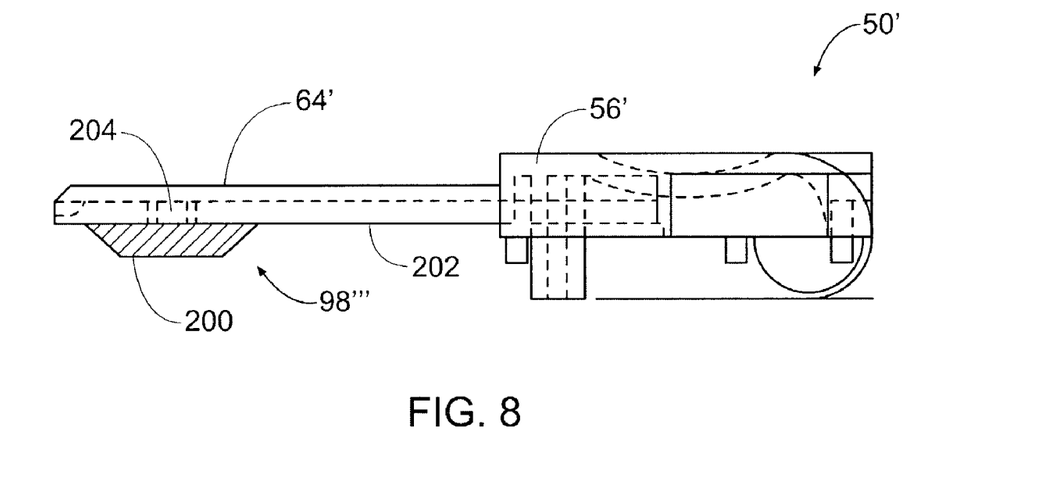
FIG. 8 is a side view of a top portion of a proximal coupler housing, which includes an integral hold down clamp feature for securing optical fibers.
Figure 9:
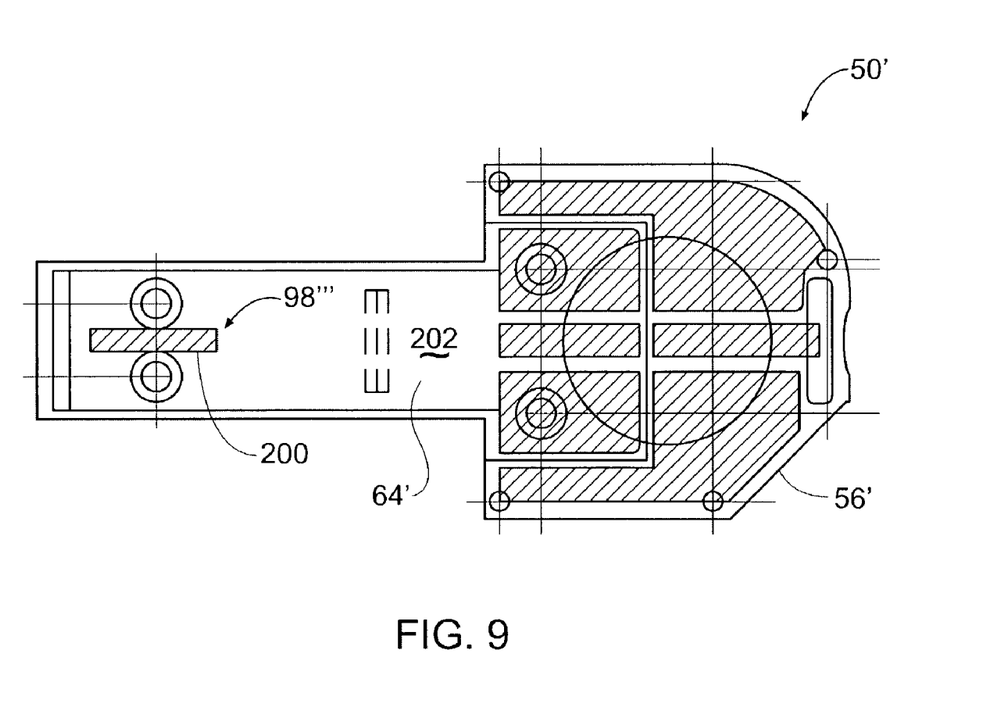
FIG. 9 is a bottom view of the proximal coupler housing shown in FIG. 8.

For example, FIG. 8 and FIG. 9 show side and bottom views, respectively, of a first portion 56' of the proximal coupler housing 50', which includes an integral hold down clamp 98''' for securing the optical fibers 76 within the channel 72 of the slide mount 52 (e.g., see FIG. 2). The clamp 98''' shown in FIG. 8 and FIG. 9 includes a projection 200, which extends outward from a surface 202 of the housing 50' cover 64' and which mates with the channel 72 of the slide mount 52. To fasten it to the housing 50', the proximal hold down clamp 98''' includes an anchor 204 (e.g., cylindrical post) that is press fit into a recess (not shown) in the cover 64' of the housing 50'. Alternatively the projection 200 is molded into housing 50', which decreases the parts count.

Following assembly of the proximal coupler, the projection 200 contacts the optical fibers 76, securing them within the channel 72. Like the separate hold down clamps described earlier, the integral hold-down clamp 98''' shown in FIG. 8 and FIG. 9 may be fabricated from materials having comparatively high modulus, including for example and without limitation, metal (e.g., aluminum, stainless steel, etc.) and engineered thermoplastics. Alternatively, the hold down clamp 98''' may also be made of resilient, comparatively low modulus materials, including thermosetting or thermoplastic elastomers, optionally containing reinforcing particles, fibers or particles and fibers.

Although preferred embodiments of the invention have been shown and described, it will be appreciated by those skilled in the art that changes may be made in these embodiments without departing from the principles and the spirit of the invention, the scope of which is defined in the appended claims. In particular, the present invention is not limited to fiber optic catheters but may be used in any application where termination of optical fibers is required. The disclosures of all articles and references, including any patent applications and publications, are hereby incorporated by reference in their entirety for all purposes.

What is claimed is:

1. A coupler for interfacing a light source and a fiber optic cable, the coupler comprising:
    a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable; and
    a clamp mounted on the slide mount adjacent to the proximal end of the slide mount, the clamp covering at least a portion of the channel, thereby securing the optical fibers in the channel.

2. The coupler of claim 1, wherein the clamp is attached to the slide mount.

3. The coupler of claim 1, further comprising a second clamp mounted on the slide mount adjacent to the distal end of the slide mount, the second clamp covering at least a portion of the channel.

4. The coupler of claim 1, further comprising a capillary tube disposed in the channel.

5. The coupler of claim 1, wherein the clamp includes a base, the base being substantially planar.

6. The coupler of claim 5, wherein the clamp further includes at least one arm that extends outward from the base.

7. A coupler for interfacing a light source and a fiber optic cable, the coupler comprising:
    a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable; and
    a clamp mounted on the slide mount adjacent to the proximal end of the slide mount, the clamp covering at least a portion of the channel, thereby securing the optical fibers in the channel,
    wherein the clamp includes a base, the base being substantially planar, and at least one arm that extends outward from the base, wherein the arm intersects the base at a non-zero angle so that at least a portion of the arm extends into the channel of the slide mount.

8. The coupler of claim 7, wherein the arm includes an elbow that contacts the optical fibers.

9. The coupler of claim 6, wherein a substantial portion of the arm lies in the same plane as the base.

10. The coupler of claim 9, wherein the arm is wider than the channel.

11. The coupler of claim 9, wherein the arm includes an arcuate portion that contacts the optical fibers in the channel.

12. A coupler for interfacing a light source and a fiber optic cable, the coupler comprising:
    a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable; and
    a clamp mounted on the slide mount adjacent to the proximal end of the slide mount, the clamp covering at least a portion of the channel, thereby securing the optical fibers in the channel, wherein the clamp includes a base, the base being substantially planar, and at least one arm that extends outward from the base, wherein a substantial portion of the arm lies in the same plane as the base, the arm is wider than the channel, and the arm includes an arcuate portion that contacts the optical fibers in the channel, and wherein the slide mount includes a transverse groove that intersects the channel and is adapted to receive the arcuare portion of the arm.

13. The coupler of claim 6, wherein the clamp further includes a pair of arms that extends outward from proximal and distal ends of the base.

14. The coupler of claim 1, further comprising a housing removably attached to the slide mount, the housing covering at least a portion of the slide mount.

15. The coupler of claim 14, wherein the clamp is an integral part of the housing.

16. A coupler for interfacing a light source and a fiber optic cable, the coupler comprising:
   a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable;
   a clamp mounted on the slide mount adjacent to the proximal end of the slide mount, the clamp covering at least a portion of the channel, thereby securing the optical fibers in the channel, and
   a housing removably attached to the slide mount, the housing covering at least a portion of the slide mount,
   wherein the clamp is an integral pan of the housing and the clamp includes a projection that extends outward from a surface of the housing, the projection adapted to be received in the channel of the slide mount.

17. The coupler of claim 15, further comprising an anchor disposed in a recess of the housing.

18. A coupler for interfacing a light source and a fiber optic cable, the coupler comprising:
   a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable;
   a capillary tube secured at or adjacent to the proximal end of the slide mount, at least a portion of the optical fibers disposed within the capillary tube, and the capillary tube disposed within the channel, thereby securing the optical fibers within the channel.

19. The coupler of claim 18, further comprising a clamp mounted on the slide mount adjacent to the distal end of the slide mount, the clamp covering at least a portion of the channel.

20. The coupler of claim 18, whereby the capillary tube is secured to the slide mount by friction means.

21. The coupler of claim 18, whereby the capillary tube is secured to the slide mount by a clamp.

22. A method of making a coupler for interfacing a light source and a fiber optic cable, the method comprising:
   providing a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable;
   disposing optical fibers in the channel of the slide mount so that the optical fibers extend from the distal end of the slide mount to the proximal end of the slide mount; and
   mounting a clamp on the slide mount adjacent to the proximal end of the slide mount, the clamp covering at least a portion of the channel and thereby securing the optical fibers within the channel.

23. A method of making a coupler for interfacing a light source and a fiber optic cable, the method comprising:
   providing a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable;
   disposing optical fibers in the channel of the slide mount so that the optical fibers extend from the distal end of the slide mount to the proximal end of the slide mount;
   disposing at least a portion of the optical fibers within a capillary tube; disposing the capillary tube within the channel; and
   securing the capillary tube at or adjacent to the proximal end of the slide mount, thereby securing the optical fibers within the channel.

24. A coupler for interfacing a laser light source and a fiber optic cable, the coupler comprising:
   a slide mount having a channel sized to receive a fiber optic cable comprised of a plurality of optical fibers, the channel extending from a point at or adjacent to the proximal end of the slide mount to a distal end of the slide mount, the proximal end of the slide mount adapted to fit into an aperture of the light source and the distal end of the slide mount adapted to transmit tight to the fiber optic cable; and
   a clamp mounted on the slide mount adjacent to the proximal end of the slide mount, the clamp covering at least a portion of the channel, thereby securing the optical fibers in the channel.

25. A coupler for interfacing a laser light source and a fiber optic cable comprised of a plurality of optical fibers, the coupler comprising:
   a slide mount having a channel sized to receive a plurality of optical fibers, the channel extending from a point at or adjacent to the proximal end of the slide mount to a distal end of the slide mount, the proximal end of the slide mount adapted to fit into an aperture of the light source and the disthi end of the slide mount adapted to transmit light to the fiber optic cable;
   a capillary tube secured at or adjacent to the proximal end of the slide mount, at least a portion of the optical fibers disposed within the capillary tube, and the capillary tube disposed within the channel, thereby securing the optical fibers within the channel.

26. A coupler for interfacing a light source and a fiber optic cable, the coupler comprising:
   a slide mount having a channel sized to receive optical fibers, the channel extending from a point at or adjacent to the proximal end of the slide mount to a distal end of the slide mount, the proximal end of the slide mount adapted to fit into an aperture of the light source and the distal end of the slide mount adapted to transmit light to the fiber optic cable;

a capillary tube secured at or adjacent to the proximal end of the slide mount, at least a portion of the optical fibers disposed within the capillary tube, and the capillary tube disposed within the channel, thereby securing the optical fibers within the channel, wherein the coupler is removable from the light source.

* * * * *

UNITED STATES PATENT AND TRADEMARK OFFICE
CERTIFICATE OF CORRECTION

| | |
|---|---|
| PATENT NO. | : 7,050,692 B2 |
| APPLICATION NO. | : 10/301937 |
| DATED | : May 23, 2006 |
| INVENTOR(S) | : Kenneth D. Harlan et al. |

It is certified that error appears in the above-identified patent and that said Letters Patent is hereby corrected as shown below:

In Claim 8, column 8, line 46, please change the word "ann" to --arm--

In Claim 12, column 9, line 10, please change the word "arcuare" to --arcuate--

In Claim 24, column 10, line 39, please change the word "tight" to --light--

In Claim 25, column 10, line 54, please change the word "disthi" to --distal--

Signed and Sealed this

Twelfth Day of September, 2006

JON W. DUDAS
*Director of the United States Patent and Trademark Office*